United States Patent [19]

Szecsi

[11] 4,246,195
[45] Jan. 20, 1981

[54] PURIFICATION OF CARBONYLATION PRODUCTS

[75] Inventor: Peter L. Szecsi, Lake Hiawatha, N.J.

[73] Assignee: Halcon Research and Development Corporation, New York, N.Y.

[21] Appl. No.: 949,345

[22] Filed: Oct. 6, 1978

[51] Int. Cl.³ .............................................. C07C 51/56
[52] U.S. Cl. .................................... 260/549; 560/232; 560/233; 568/484; 568/492
[58] Field of Search ......... 260/549, 604 HF, 604 AC; 560/232, 233

[56] References Cited

U.S. PATENT DOCUMENTS 1,986,322   1/1935   Clouzeaur ............................ 260/549

Primary Examiner—Paul J. Killos
Attorney, Agent, or Firm—William C. Long; David Dick; Riggs T. Stewart

[57] ABSTRACT

Carbonylation products of methyl acetate such as acetic anhydride are purified with respect to iodine contaminants by treatment with cesium acetate, potassium acetate or sodium acetate.

4 Claims, No Drawings

PURIFICATION OF CARBONYLATION PRODUCTS

This invention relates to the purification of carbonylation products and is more particularly concerned with the purification of acetic anhydride.

In recent years there have been developed processes for the carbonylation of methyl acetate under anhydrous conditions in the presence of a Group VIII metal and in the presence of an iodine moiety, generally methyl iodide. Processes of this type to produce acetic anhydride are described, for example in U.S. Pat. Nos. 4,002,677 and 4,002,678 of Jan. 11, 1977 and in U.S. Pat. No. 4,115,444 of Sep. 19, 1978 as well as in British Pat. No. 1,468,940. Other carbonylation products such as acetaldehyde and ethylidene diacetate are also produced when the anhydrous carbonylation process is carried out in the presence of substantial amounts of hydrogen as described, for example in Belgian Pat. No. 839,321. As pointed out in these disclosures, dimethyl ether can be substituted for part or all of the methyl acetate.

These carbonylation products are eventually separated and recovered from the carbonylation reaction mixture by distillation during which the iodine moieties, largely in the form of methyl iodine or acetyl iodide, are removed and returned to the carbonylation zone to provide the iodine moiety required in the production of further quantities of carbonylation products of the character referred to above. It has been found, however, that very small quantities of organic iodine compounds, such as the above-mentioned methyl iodide and acetyl iodide as well as other iodine compounds formed in the course of the carbonylation reaction, remain present in the carbonylation products. While the amounts of such organic iodine compounds are very small, yet they contaminate the products to an extent which is undesirable in many cases and frequently interferes with their utilization. Attempts to eliminate or reduce the quantities of these compounds to acceptable levels by fractional distillation have not been successful and the problem caused by this contamination remains.

It is, accordingly, an object of this invention to provide a process for effectively removing iodine moieties from carbonylation products produced by the anhydrous carbonylation of methyl acetate.

In accordance with the invention, it has been surprisingly discovered that when the carbonylation product to be purified is treated with a very restricted class of salts under moderate temperature conditions and for a relatively short time, the organic iodine moieties present as contaminants in the carbonylation product can be converted to an inorganic form which is essentially non-volatile and from which the carbonylation product can be readily separated by techniques such as volatilization of the carbonylation products by simple flash vaporization or fractional distillation, and the relatively non-volatile, inorganic iodine compounds remain behind. Other processes have, to some extent, been faced with similar difficulties although arising in quite different contexts and the chemical treatments of organic compounds or reaction mixtures to remove various halogen values has been heretofore proposed. For example, in Kollar U.S. Pat. No. 3,884,965, acyloxylation reaction products such as glycol esters are freed from halogen compound contaminants, especially bromine compounds, by bringing them into contact with compounds of various metals including alkali metals, alkaline earth metals, zinc, lead, cadmium, tin, mercury, silver, manganese, copper, nickel, cobalt, iron and chromium. These metals can be used as oxides, hydroxides, carbonates, bicarbonates, salts of mineral acids, benzoates, napthenates and other carboxylic acid salts. Sherwin et al. U.S. Pat. No. 4,087,623 is concerned with the recovery of elemental iodine from an acyloxylation mixture of the type involved in Kollar, U.S. Pat. No. 3,884,965 produced by the molecular oxygen oxidation of propylene in the presence of iodine and a tellurium catalyst. Sherwin et al. propose a multistep process which eventually produces the liberated iodine in a form suitable for recycling. In the course of the process, an iodine-rich cut from the distilled acyloxylation mixture is treated with a Group IA metal compound. This cut contains a large proportion of the total iodine content of the system, i.e, it contains a significant percentage of iodine.

The present invention on the contrary, not only deals with the purification of carbonylation products, rather than acyloxylation products, but with the purification of such products containing only very small amounts of iodine contaminants, readily expressed in parts per million (ppm), and it has been discovered that only a very small class of metal compounds is effective for the desired purpose. Thus, in accordance with this invention, it has been found that the treating agents effective to remove very small amounts of iodine moieties from carbonylation products produced by the anhydrous carbonylation of methyl acetate with carbon monoxide, or mixtures of carbon monoxide and hydrogen, in the presence of a Group VIII metal and an iodine moiety, are the acetates of sodium, potassium and cesium. Attempts to use the closely-related alkaline earth metal salts such as magnesium and barium acetates were unsuccessful and even the alkali metal lithium is far less effective, contrary to what would be expected from the prior art.

The process of this invention is preferably carried out in a substantially water-free system. In such a system, the occurrence of the observed reaction takes place in a medium wherein hydrolysis of the organic iodine compounds is largely precluded.

The carbonylation product feed to the process of this invention is one which consists essentially of acetic anhydride and/or acetaldehyde and/or ethylidene diacetate and/or vinyl acetate and which contains organoiodine compound impurities corresponding to or derived from the iodine moieties present in the carbonylation zone wherein the carbonylation feed is produced by the anhydrous carbonylation of methyl acetate in the presence of a Group VIII metal as described in the above-mentioned U.S. Pat. Nos. 4,002,677, 4,002,678, 4,115,444, British Pat. No. 1,468,940 and Belgian patent 839,321, the disclosures of which U.S., British and Belgian patents are incorporated herein by reference. The feed is preferably, as mentioned, substantially water-free, i.e., containing under 500 ppm by wt. of water.

The organic iodine impurity content of the carbonylation product feed to the process of the invention can vary, the limiting factor on the impurity level in the feed being essentially an economic one. Complete removal of impurities from the feed by distillation prior to application of the process of this invention is generally uneconomic and, practically speaking, has not been found to be feasible. However, the greater the content of organic iodine compounds in the feed to the process of this invention the greater the amount of treating agent required. In each case, therefore, the impurity level in the feed involves an economic balance between cost of prior distillation and value of the treating agent. Such considerations normally dictate feeds containing under 1000 ppm of soluble organic iodine compounds in the feed, generally less than 500 ppm and usually at most 200 ppm, all amounts referring to contained organic halogen, based on total feed. Most commonly, but not essentially, the carbonylation product feed to the process of this invention will contain 100 to 200 ppm (weight basis) of organic iodine, based on total feed.

Reduction or substantial elimination of the organo-iodine content of the carbonylation product feed is accomplished by introducing the feed into contact with a treating agent of the character described above under conditions promoting reaction between the organo-iodine compounds and the treating agent, thereby converting, at least in part, the organic iodine compounds to inorganic non-volatile compounds.

The process of this invention is most suitably carried out in homogeneous liquid phase systems or in heterogeneous liquid-phase systems.

The process of this invention comprises admixing the treating agent and the carbonylation product feed, maintaining them in contact for a period of time sufficient to cause interaction between the treating agent and at least a portion of the organo-iodine impurities in the feed, and then separating the carbonylation product from the non-volatile iodine compound. The contacting can be accomplished over relatively broad temperature ranges. When the feed is in the liquid phase, appreciable reduction in organo-iodine compound impurity level is encountered at temperatures as low as about 75° C., but most desirably at temperatures of approximately 100° C. or above. It is preferred to employ temperatures of at least about 120° C. Upper limits on temperature, however, are not dictated by the unusual considerations but involve such factors as minimization of thermal degradation of the feed. Accordingly, temperatures in excess of 175° C. would seldom be used.

The period of time which the feed and the treating agent are permitted to remain in contact influences to some extent the amount of organo-iodine compound that will be converted to nonvolatile form. In liquid phase operations, significant conversion is achieved with periods of time of even as little as a few minutes. Greater contact times promote increased conversion of organo-iodine compound, and when the carbonylation product feed is in the liquid phase, it is accordingly desired to operate with contact times of at least 3 minutes and it is preferred to operate with contact times of at least 15 minutes.

There is no process-dictated upper limit on contact time. The only factor of significance in assessing such maxima relates to the economics involved in providing equipment capable of providing long contact times. Accordingly, contact times of a matter of hours are entirely suitable for the practice of this invention, independent of the phase of the feed. However, economic considerations normally would indicate employment of shorter contact times and it would seldom be economic to provide for contact times in excess of 5 hours.

As used herein, contact time in a batch system is the period during which the treating agent and the feed are maintained in contact with each other at reaction conditions. In continuous operation, contact time (in hours or fractions thereof) is defined as the volume of the vessel wherein the contact takes place divided by the total volume of organic material fed to the reactor (measured at actual conditions) per hour.

As hereinabove indicated, neither temperature nor contact time is of particular criticality to the process of this invention. On the other hand, it has been found essential that the amount and nature of the treating agent employed must be such as to provide, during the contacting, a ratio of equivalents of metal salt to equivalents of total iodine which is in excess of 1:1, preferably at least 1.1:1. The higher this ratio, the more extensive will be the degree of conversion of organo-iodine compound impurities and the faster will be the rate of reaction. Accordingly, it is desired to employ ratios which are at least 2:1 and which are preferably at least 4:1. There is, however, no process limit on the upper level of this ratio and, dependent upon economics and the type of equipment employed, it is both feasible and often desirable to employ systems which give ratios of 100:1 or even more.

By operating in the manner described above, significant reductions in impurities level in the carbonylation feed are obtained. The extend of reduction (expressed as equivalents of iodine present as organic compounds in the feed prior to treatment minus the equivalents of iodine present as organics in the product after treatment, the difference being divided by the total equivalents of such iodine in the feed) is hereinafter referred to as "conversion." Under preferred conditions outlined above, it is readily possible to obtain conversions exceeding 50% and often possible to obtain conversions exceeding 70%. With liquid phase feeds, when operating with ratios of treating agent to total iodine in excess of 4:1, at temperatures exceeding 100° C. and for contact time in excess of 5 minutes, conversions of the order of 70 to 90% or even higher are commonly obtained.

The form of the contacting zone is not critical to the conduct of the process of this invention. Thus, it can be simply of a large tank providing the requisite retention time or it can be equipped with one or more agitators to promote uniformity of mixing.

The following examples of specific application will serve to provide a fuller understanding of the invention but it will be understood that these examples are given for illustrative purposes only, however, and are not to be interpreted as limitative of the invention.

EXAMPLE 1

A glass ampule was charged with 15 g. of acetic anhydride containing 116 ppm methyl iodide and 0.0211 g. anhydrous potassium acetate was added to give a salt to I mole ratio of 17.5. The ampule was sealed, placed inside a stainless-steel pipe bomb which was then immersed in an oil bath and heated at 150° C. for 2 hours. After cooling to room temperature, the ampule was opened and the homogeneous effluent was analyzed for residual methyl iodide by gas chromatography (GC). No detectable amount was found when so analyzed. The effluent was then distilled at atmospheric pressure to recover volatile material from the non-volatile iodide salt.

EXAMPLE 2

Example 1 was repeated but cesium acetate in a salt to I mole ratio of 17 was employed as the treating agent. As in Example 1, no methyl iodide was detected when the effluent was subjected to G.C. analysis.

EXAMPLE 3

Example 1 was again repeated but sodium acetate in a salt to I mole ratio of 18.9 was used instead of potassium acetate. G.C. analysis detected the presence of only 2 ppm of methyl iodide.

COMPARATIVE EXAMPLE A

Again repeating Example 1, lithium acetate in a salt to I mole ratio of 18.6 was substituted for the potassium acetate. G.C. analysis showed a methyl iodide content of 63 ppm.

EXAMPLE 4

Following the procedure of Example 1, a glass ampule was charged with 15 g. of a mixture of 72 weight percent acetic anhydride, 20 weight percent acetic acid and 8 weight percent vinyl acetate containing 100 ppm methyl iodide and anhydrous potassium acetate was added to give a salt to I mole ratio of 20. The ampule was sealed, placed inside a stainless-steel pipe bomb which was then immersed in an oil bath and heated at 150° C. for 2 hours. After cooling to room temperature, the ampule was opened and the homogeneous effluent was analyzed for residual methyl iodide by gas chromatography (GC). A content of 6 ppm of methyl iodide was found when so analyzed. The effluent was then distilled at atmospheric pressure to recover volatile material from the nonvolatile iodide salt.

EXAMPLE 5

Example 4 was repeated except that the potassium acetate was replaced by sodium acetate in a salt to I mole ratio of 20. G.C. analysis showed a methyl iodide content of 10 ppm.

EXAMPLE 6

Example 4 was again repeated but this time the potassium acetate was replaced by cesium acetate in a salt to I mole ratio of 20. G.C. analysis did not detect any methyl iodide.

COMPARATIVE EXAMPLE B

Example 4 was again repeated but the potassium acetate was replaced by lithium acetate in a salt to I ratio of 20. When analyzed by G.C. a methyl iodide content of 24 ppm was found.

COMPARATIVE EXAMPLE C

Replacing potassium acetate by barium acetate in a salt to I ratio of 20, Example 4 was repeated. A methyl iodide content of 65 ppm was found by G.C. analysis.

COMPARATIVE EXAMPLE D

This time replacing the potassium acetate by magnesium in a salt to I mole ratio of 20, Example 4 was repeated. G.C. analysis showed a methyl iodide content of 72.

EXAMPLE 7

Again following the procedure of Example 4, a glass ampule was charged with 15 g. of acetic anhydride containing 116 ppm methyl iodide and anhydrous potassium acetate was added to give a salt to I mole ratio of 9.8. The ampule was sealed, placed inside a stainless-steel pipe bomb which was then immersed in an oil bath and heated at 150° C. for 2 hours. After cooling to room temperature, the ampule was opened and the homogeneous effluent was analyzed for residual methyl iodide by gas chromatography (GC). No detectable amount of methyl iodide was found when so analyzed. The effluent was then distilled at atmospheric pressure to recover volatile material from the non-volatile iodide salt.

EXAMPLE 8

Example 7 was repeated except that the potassium acetate was replaced by sodium acetate in a salt to I mole ratio of 9.7 G.C. analysis showed a methyl iodide content of 10 ppm.

EXAMPLE 9

Example 7 was again repeated but the potassium acetate was replaced by cesium acetate in a salt to I mole ratio of 10. G.C. analysis did not detect any methyl iodide.

COMPARATIVE EXAMPLE E

When Example 7 was repeated with lithium acetate in a salt to I ratio of 9.8 being used as the treating salt rather than potassium acetate, G.C. analysis of the effluent showed a content of methyl iodide of 72 ppm.

What is claimed is:

1. A process for the purification of methyl acetate carbonylation products produced by the reaction of carbon monoxide upon methyl acetate in the presence of a Group VIII noble metal and an iodine moiety, optionally also in the presence of hydrogen, to remove organic iodine contaminants including methyl iodide therefrom which comprises treating said products with a small but effective amount of a treating agent which is cesium acetate, potassium acetate or sodium acetate to form inorganic salts from the iodine in said organic contaminants, and separating said carbonylation products from said salts.

2. A process as defined in claim 1, wherein said carbonylation products contain less than 1000 ppm of said organic iodine contaminants.

3. A process as defined in claim 1, wherein said treating agent is used in an amount of at least 1 equivalent per equivalent of total I in the carbonylation products.

4. A process as defined in claim 1, wherein the quantity of iodine contaminant is reduced to at most about 10 ppm.

* * * * *

UNITED STATES PATENT AND TRADEMARK OFFICE
CERTIFICATE OF CORRECTION

PATENT NO. : 4,246,195
DATED : January 20, 1981
INVENTOR(S) : Peter L. Szecsi

It is certified that error appears in the above—identified patent and that said Letters Patent is hereby corrected as shown below:

Column 1, line 27, "iodine" should be --iodide--

Column 3, line 38, "unusual" should be --usual process--

Column 4, line 23, "extend" should be --extent--

Signed and Sealed this

Sixteenth Day of February 1982

[SEAL]

Attest:

GERALD J. MOSSINGHOFF

Attesting Officer    Commissioner of Patents and Trademarks